United States Patent
Jähne et al.

(10) Patent No.: US 6,476,059 B1
(45) Date of Patent: *Nov. 5, 2002

(54) USE OF POLYCYCLIC 2-AMINOTHIAZOLE SYSTEMS FOR THE TREATMENT OF OBESITY

(75) Inventors: Gerhard Jähne, Frankfurt (DE); Karl Geisen, Frankfurt (DE); Hans-Jochen Lang, Hofheim (DE); Martin Bickel, Bad Homburg (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/501,209

(22) Filed: Feb. 10, 2000

(30) Foreign Application Priority Data

Feb. 26, 1999 (DE) .......................... 199 08 537

(51) Int. Cl.$^7$ .................. A61P 3/04; A61K 31/429; A61K 9/20; A61K 9/48; A61K 9/02
(52) U.S. Cl. .................. 514/366; 514/909; 424/451; 424/464; 424/474; 424/436
(58) Field of Search ................. 514/909, 338, 514/366; 546/270.1; 548/150; 424/451, 464

(56) References Cited

U.S. PATENT DOCUMENTS

| 3,507,868 A | 4/1970 | Manning ............ 260/251 |
| 6,251,922 B1 * | 6/2001 | Jahne et al. ........... 514/338 |

FOREIGN PATENT DOCUMENTS

| DE | 26 40 358 | 3/1978 |
| EP | 0 230 334 | 7/1987 |
| EP | 0 432 040 | 6/1991 |
| WO | 00/04006 | 1/2000 |

OTHER PUBLICATIONS

R. Gupta et al., "Synthesis and antiinflammatory activity of some substituted 2–amino–8H–ideno [1, 2–d] thiazoles", Indian J. Pharm. Sci., 1992, 53, pp. 245–248.
P. Lyle, "Iontophoretic Devices for Drug Delivery", Pharmaceutical Research, 1986, 3 (6): pp. 318–326.
N. Miyaura et al., "Palladium–Catalyzed Cross–Coupling Reactions of Organoboron Compounds", Chem. Rev., 1995, 95, pp. 2457–2483.
Takayuki Oh–e et al., "Palladium–Catalyzed Cross–Coupling Reaction of Organoboron Compounds with Organic Triflates", J. Org. Chem., 1993, 58, pp. 2201–2208.
K. Sonagashira et al., "A Convenient Synthesis of Acetylenes: Catalytic Substitutions of Acetylenic Hydrogen with Bromoalkenes, Iodoarenes, and Bromopyridines", 1975, Tetrahedron Lett., pp. 4467–4470.
S. Takahashi et al., "A Convenient Synthesis of Ethynylarenes and Dietthynlarenes", 1980, Synthesis, pp. 627–630.
E. Negishi et al., "Direct Synthesis of Terminal Alkynes via Pd–Catalyzed Cross coupling of Aryl and Alkenyl Halides with Ethynlmetals Containing Zn, Mg, and Sn. Critical Comparison of Countercations", 1997, J. Org. Chem., 62, pp. 8957–8960.
A. Hassner et al., "Charge–shift Probes of Membrane Potential. Synthesis", 1984, J. Org. Chem., 49, pp. 2546–2551.
Gupta et al.; "Synthesis and Antiinflammatory Activity of Some Substituted 2 Amino–8H–Indeno [1,2–d] Thiazoles"; Indian Journal of Pharmaceutical Science; Nov.–Dec. 1991; pp. 245–248; XP–000925078.
Ramalingam et al.; "Synthesis and Antimicrobial Activity of Azasteroid–Type Compounds and Related Systems. Effect of Hydrophilic and Lipophilic Groups on Activity"; Journal of Medical Chemistry; vol. 20, No. 5; 1977; pp. 661–669; XP–000915411.
Khazi et al.; "Synthesis and Biological Activity of Some 2–Amino/Arylamino–4H–(1) Benzothiopyrano [4,3–d] Thiazoles"; Indian Journal of Heterocyclic Chemistry; vol. 4; Apr.–Jun. 1995; pp. 243–248; XP–000933945.

* cited by examiner

*Primary Examiner*—Edward J. Webman
*Assistant Examiner*—Helen Nguyen
(74) *Attorney, Agent, or Firm*—Heller Ehrman White and McAuliffe

(57) ABSTRACT

The invention relates to the use of polycyclic 2-aminothiazole systems and their physiologically tolerated salts and physiologically functional derivatives for the treatment of obesity.

The treatment involves administration of a compound of formula I,

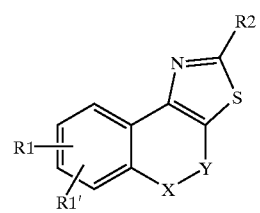

in which the radicals have the stated meanings, and of their physiologically tolerated salts and physiologically functional derivatives.

29 Claims, No Drawings

USE OF POLYCYCLIC 2-AMINOTHIAZOLE SYSTEMS FOR THE TREATMENT OF OBESITY

BACKGROUND OF THE INVENTION

The invention relates to the use of polycyclic 2-aminothiazole systems and of their physiologically tolerated salts and physiologically functional derivatives for producing medicines for the prophylaxis or treatment of obesity.

2-Aminothiazole systems are described as anti-inflammatory substances in R. Gupta et al., Indian J. Pharm. Sci. 1991, 53, 245–248.

The invention was based on the object of providing compounds which display a therapeutically utilizable anorectic effect.

SUMMARY OF THE INVENTION

The invention relates to a method for the treatment of obesity comprising administering to a patient in need of such treatment a pharmaceutical composition comprising a pharmaceutically acceptable carrier and a compound of formula I:

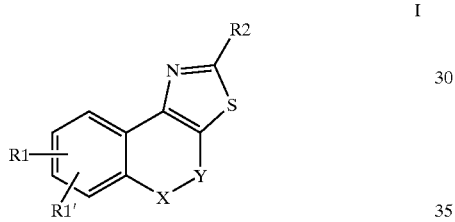

in which
Y is a direct linkage, $CH_2$ or $CH_2$—$CH_2$;
X is $CH_2$, O, NH, NR6 or S;
R1, R1' are independently H, F, Cl, Br, I, $CF_3$, CN, $NO_2$, COOH, COO($C_1$–$C_6$)alkyl, $CONH_2$, CONH($C_1$–$C_6$)alkyl, CON[($C_1$–$C_6$)alkyl]$_2$, ($C_1$–$C_6$)-alkyl, ($C_2$–$C_6$)-alkenyl, ($C_2$–$C_6$)-alkynyl, O—($C_1$–$C_6$)-alkyl (where one, more than one or all hydrogen(s) in the alkyl, alkenyl and alkynyl radicals may be replaced by fluorine, or one hydrogen may be replaced by OH, $OC(O)CH_3$, $OC(O)H$, O—$CH_2$—Ph, $NH_2$, NH—CO—$CH_3$ or $N(COOCH_2Ph)_2$), $SO_2$—$NH_2$, $SO_2NH(C_1$–$C_6)$-alkyl, $SO_2N[(C_1$–$C_6)$-alkyl]$_2$, S—($C_1$–$C_6$)-alkyl, S—$(CH_2)_n$-phenyl, SO—($C_1$–$C_6$)-alkyl, SO—$(CH_2)$,-phenyl, $SO_2$—($C_1$–$C_6$)-alkyl, $SO_2$—$(CH_2)_n$-phenyl (where n is 0–6 and the phenyl radical may be optionally substituted up to two times by F, Cl, Br, OH, $CF_3$, $NO_2$, CN, $OCF_3$, O—($C_1$–$C_6$)-alkyl, ($C_1$–$C_6$)-alkyl or $NH_2$), $NH_2$, NH—($C_1$–$C_6$)-alkyl, N(($C_1$–$C_6$)-alkyl)$_2$, NH($C_1$–$C_7$)-acyl, phenyl, biphenylyl, O—$(CH_2)_n$-phenyl (where n is 0–6), 1- or 2-naphthyl, 2-, 3- or 4-pyridyl, 2- or 3-furanyl, 2- or 3-thienyl (wherein the phenyl, biphenylyl, naphthyl, pyridyl, furanyl or thienyl rings may be optionally substituted up to 3 times by F, Cl, Br, I, OH, $CF_3$, $NO_2$, CN, $OCF_3$, O—($C_1$–$C_6$)-alkyl, ($C_1$–$C_6$)-alkyl, $NH_2$, NH($C_1$–$C_6$)-alkyl, N(($C_1$–$C_6$)-alkyl)$_2$, $SO_2$—$CH_3$, COOH, COO—($C_1$–$C_6$)-alkyl or $CONH_2$), 1,2,3-triazol-5-yl (wherein triazol ring may be optionally substituted in position 1, 2 or 3 by methyl or benzyl) or tetrazol-5-yl (wherein the tetrazol ring may be optionally substituted in position 1 or 2 by methyl or benzyl);
R2 is $NH_2$, NHR3 or NR4R5, wherein
R3 is ($C_1$–$C_6$)alkyl, CN, CHO, CO—$NH_2$, CH=NH, C(S)—$NH_2$, C(=NH)—NH-phenyl (wherein the phenyl ring may be optionally substituted up to two times by F, Cl, Br, I, OH, $CF_3$, $NO_2$, CN, $OCF_3$, O—($C_1$–$C_6$)-alkyl, ($C_1$–$C_6$)-alkyl, $NH_2$, NH($C_1$–$C_6$)-alkyl, N(($C1$–$C6$)-alkyl)$_2$, $SO_2$—$CH_3$, COOH, COO—($C_1$–$C_6$)-alkyl or $CONH_2$), phenyl, $CH_2$-phenyl (wherein the phenyl ring may be optionally substituted up to 3 times by F, Cl, Br, I, OH, $NO_2$, CN, $OCF_3$, O—($C_2$–$C_6$)-alkyl, ($C_2$–$C_6$)-alkyl, $NH_2$, NH($C_1$–$C_6$)-alkyl, N(($C_1$–$C_6$)-alkyl)$_2$, $SO_2$—$CH_3$, COOH, COO—($C_1$–$C_6$)-alkyl or $CONH_2$), biphenylyl, 1- or 2-naphthyl, 4-pyridyl, 2- or 3-furanyl, 2- or 3- thienyl, 5-tetrazolyl (wherein the biphenylyl, naphthyl, pyridyl, furanyl or thienyl rings may be optionally substituted up to two times by F, Cl, Br, I, OH, $CF_3$, $NO_2$, CN, $OCF_3$, O—($C_1$–$6_6$)-alkyl, ($C_1$–$C_6$)-alkyl, $NH_2$, NH($C_1$–$C_6$)-alkyl, N(($C_1$–$C_6$)-alkyl)$_2$, $SO_2$—$CH_3$, COOH, COO—($C_1$–$C_6$)-alkyl or $CONH_2$), $CH_2$-phenyl, $CH_2$-2-pyridyl or $CH_2$-4-pyridyl (wherein the phenyl or pyridyl ring may be optionally substituted once or twice by F, Cl, Br, I, OH, $CF_3$, $NO_2$, CN, $OCF_3$, O—($C_1$–$C_6$)-alkyl, ($C_1$–$C_6$)-alkyl, $NH_2$, NH($C_1$–$C_6$)-alkyl, N(($C_1$–$C_6$)-alkyl)$_2$ $SO_2$—$CH_3$, COOH, COO—($C_1$–$C_6$)-alkyl or $CONH_2$);
R4 is $C_1$–$C_6$-alkyl, $C_3$–$C_6$-cycloalkyl, $C_2$–$C_6$-alkenyl, $C_3$–$C_6$-alkynyl, phenyl or $CH_2$-phenyl (wherein the phenyl ring may be optionally substituted once or twice by F, Cl, Br, I, OH, $CF_3$, $NO_2$, CN, $OCF_3$, O—($C_1$–$C_6$)-alkyl, ($C_1$–$C_6$)-alkyl, $NH_2$, NH($C_1$–$C_6$)-alkyl, N(($C_1$–$C_6$)-alkyl)$_2$, $SO_2$—$CH_3$, COOH, COO—($C_1$–$C_6$)-alkyl or $CONH_2$);
R5 is H, $C_1$–$C_6$-alkyl, $C_3$–$C_6$-cycloalkyl, $C_2$–$C_6$-alkenyl, $C_3$–$C_6$-alkynyl, phenyl or $CH_2$-phenyl (wherein the phenyl ring may be optionally substituted once or twice by F, Cl, Br, I, OH, $CF_3$, $NO_2$, CN, $OCF_3$, O—($C_1$–$C_6$)-alkyl, ($C_1$–$C_6$)-alkyl, $NH_2$, NH($C_1$–$C_6$)-alkyl, N(($C_1$–$C_6$)-alkyl)$_2$, $SO_2$—$CH_3$, COOH, COO—($C_1$–$C_6$)-alkyl or $CONH_2$) or
R4 and R5 together form one of the groups $CH_2$—$CH_2$—$CH_2$—$CH_2CH_2$, $CH_2$—$CH_2$—$N(CH_3)$—$CH_2$—$CH_2$, $CH_2$—$CH_2$—$N(CH_2$-phenyl)—$CH_2$—$CH_2$, $CH_2$—$CH_2$—O—$CH_2$—$CH_2$ or $CH_2$—$CH_2$—$CH_2$—$CH_2$;
R6 is ($C_1$–$C_6$)alkyl, acyl, (C=O)—($C_1$–$C_6$)alkyl, (C=O)-($C_3$–$C_6$)-cycloalkyl, phenyl, naphthyl, pyridyl, —$SO_2$-phenyl, or $SO_2$-naphthyl;
and their physiologically tolerated salts and physiologically functional derivatives.

DETAILED DESCRIPTION OF THE PREFERRED EMBODIMENTS

The present invention is directed to a method of treating obesity which encompasses prophylaxis and amelioration of obesity comprising administering to a patient in need thereof a pharmaceutical composition comprising a compound of formula I:

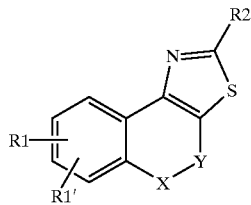

in which
Y is a direct linkage, $CH_2$ or $CH_2$—$CH_2$;
X is $CH_2$, O, NH, NR6 or S;
R1, R1' are independently H, F, Cl, Br, I, $CF_3$, CN, $NO_2$, COOH, COO($C_1$–$C_6$)alkyl, $CONH_2$, CONH($C_1$–$C_6$) alkyl, CON[($C_1$–$C_6$)alkyl]$_2$, ($C_1$–$C_6$)-alkyl, ($C_2$–$C_6$)-alkenyl, ($C_2$–$C_6$)-alkynyl, O—($C_1$–$C_6$)-alkyl (where one, more than one or all hydrogen(s) in the alkyl, alkenyl and alkynyl radicals may be replaced by fluorine, or one hydrogen may be replaced by OH, $OC(O)CH_3$, $OC(O)H$, O—$CH_2$—Ph, $NH_2$, NH—CO—$CH_3$ or $N(COOCH_2Ph)_2$), $SO_2$—$NH_2$, $SO_2NH(C_{1-6})$-alkyl $SO_2N[(C_1$–$C_6)$-alkyl]$_2$, S—($C_1$–$C_6$)-alkyl, S—($CH_2$)$_n$-phenyl, SO—($C_1$–$C_6$)-alkyl, SO—($CH_2$)$_n$-phenyl, $SO_2$—($C_1$–$C_6$)-alkyl, $SO_2$—$(CH)_n$-phenyl (where n is 0–6 and the phenyl radical may be optionally substituted up to two times by F, Cl, Br, OH, $CF_3$, $NO_2$, CN, $OCF_3$, O—($C_1$–$C_6$)-alkyl, ($C_1$–$C_6$)-alkyl or $NH_2$), $NH_2$, NH—($C_1$–$C_6$)-alkyl, N(($C_1$–$C_6$)-alkyl)$_2$, NH($C_1$–$C_7$)-acyl, phenyl, biphenylyl, O—($CH_2$)$_n$-phenyl (where n is 0–6), 1- or 2-naphthyl, 2-, 3- or 4-pyridyl, 2- or 3-furanyl, 2- or 3-thienyl (wherein the phenyl, biphenylyl, naphthyl, pyridyl, furanyl or thienyl rings may be optionally substituted up to 3 times by F, Cl, Br, I, OH, $CF_3$, $NO_2$, CN, $OCF_3$, O—($C_1$–$C_6$)-alkyl, ($C_1$–$C_6$)-alkyl, $NH_2$, NH($C_1$–$C_6$)-alkyl, N(($C_1$–$C_6$)-alkyl)$_2$, $SO_2$—$CH_3$, COOH, COO—($C_1$–$C_6$)-alkyl or $CONH_2$), 1,2,3-triazol-5-yl (wherein triazol ring may be optionally substituted in position 1, 2 or 3 by methyl or benzyl) or tetrazol-5-yl (wherein the tetrazol ring may be optionally substituted in position 1 or 2 by methyl or benzyl);
R2 is $NH_2$, NHR3 or NR4R5, wherein
  R3 is ($C_1$–$C_6$)alkyl, CN, CHO, CO—$NH_2$, CH=NH, C(S)—$NH_2$, C(=NH)—NH-phenyl (wherein the phenyl ring may be optionally substituted up to two times by F, Cl, Br, I, OH, $CF_3$, $NO_2$, CN, $OCF_3$, O—($C_1$–$C_6$)-alkyl, ($C_1$–$C_6$)-alkyl, $NH_2$, NH($C_1$–$C_6$)-alkyl, N(($C_1$–$C_6$)-alkyl)$_2$, $SO_2$—$CH_3$, COOH, COO—($C_1$–$C_6$)-alkyl or $CONH_2$), phenyl, $CH_2$-phenyl (wherein the phenyl ring may be optionally substituted up to 3 times by F, Cl, Br, I, OH, $NO_2$, CN, $OCF_3$, O—($C_2$–$C_6$)-alkyl, ($C_2$–$C_6$)-alkyl, $NH_2$, NH($C_1$–$C_6$)-alkyl, N(($C_1$–$C_6$)-alkyl)$_2$, $SO_2$—$CH_3$, COOH, COO—($C_1$–$C_6$)-alkyl or $CONH_2$), biphenylyl, 1- or 2-naphthyl, 4-pyridyl, 2- or 3-furanyl, 2- or 3- thienyl, 5-tetrazolyl (wherein the biphenylyl, naphthyl, pyridyl, furanyl or thienyl rings may be optionally substituted up to two times by F, Cl, Br, I, OH, $CF_3$, $NO_2$, CN, $OCF_3$, O—($C_{1-6}$)-alkyl, ($C_1$–$C_6$) $NH_2$, NH($C_1$–$C_6$)-alkyl, N(($C_1C_6$)-alkyl)$_2$, $SO_2$—$CH_3$, COOH, COO—($C_1$–$C_6$)-alkyl or $CONH_2$), $CH_2$-phenyl, $CH_2$-pyridyl or $CH_2$-4-pyridyl (wherein the phenyl or pyridyl ring may be optionally substituted once or twice by F, Cl, Br, I, OH, $CF_3$, $NO_2$, CN, $OCF_3$, O—($C_1$–$C_6$)-alkyl, ($C_1$–$C_6$)-alkyl, $NH_2$, NH($C_1$–$C_6$-alkyl, N(($C_1$–$C_1$–$C_6$)-alkyl)$_2SO_2$—$CH_3$, COOH, COO—($C_1$–$C_6$)-alkyl or $CONH_2$);
  R4 is $C_1$–$C_6$-alkyl, $C_3$–$C_6$-cycloalkyl, $C_2$–$C_6$-alkenyl, $C_3$–$C_6$-alkynyl, phenyl or $CH_2$-phenyl (wherein the phenyl ring may be optionally substituted once or twice by F, Cl, Br, I, OH, $CF_3$, $NO_2$, CN, $OCF_3$, O—($C_1$–$C_6$)-alkyl, ($C_1$–$C_6$)-alkyl, $NH_2$, NH($C_1$–$C_6$)-alkyl, N(($C_1$–$C_6$)-alkyl)$_2$, $SO_2$—$CH_3$, COOH, COO—($C_1$–$C_6$)-alkyl or $CONH_2$);
  R5 is H, $C_1$–$C_6$-alkyl, $C_3$–$C_6$-cycloalkyl, $C_2$–$C_6$-alkenyl, $C_3$–$C_6$-alkynyl, phenyl or $CH_2$-phenyl (wherein the phenyl ring may be optionally substituted once or twice by F, Cl, Br, I, OH, $CF_3$, $NO_2$, CN, $OCF_3$, O—($C_1$–$C_6$)-alkyl, ($C_1$–$C_6$)-alkyl, $NH_2$, NH($C_1$–$C_6$)-alkyl, N(($C_1$–$C_6$)-alkyl)$_2$, $SO_2$—$CH_3$, COOH, COO—($C_1$–$C_6$)-alkyl or $CONH_2$) or
  R4 and R5 together form one of the groups $CH_2$—$CH_2$—$CH_2$—$CH_2CH_2$, $CH_2$—$CH_2$—$N(CH_3)$—$CH_2$—$CH_2$, $CH_2$—$CH_2$—$N(CH_2$-phenyl)—$CH_2$—$CH_2$, $CH_2$—$CH_2$—O—$CH_2$—$CH_2$ or $CH_2$—$CH_2$—$CH_2$—$CH_2$;
  R6 is ($C_1$–$C_6$)alkyl, acyl, (C=O)-($C_1$–$C_6$)alkyl, (C=O)—($C_3$–$C_6$)-cycloalkyl, phenyl, naphthyl, pyridyl, —$SO_2$-phenyl, or $SO_2$-naphthyl;
and their physiologically tolerated salts and physiologically functional derivatives.

A preferred embodiment encompasses treating obesity with a pharmaceutical composition comprising a compound of formula I wherein:
Y is a direct linkage, $CH_2$ or $CH_2$—$CH_2$;
x is $CH_2$ or O;
R1 is F, Cl, Br, I, $CF_3$, CN, $NO_2$, COOH, COO($C_1$–$C_6$) alkyl, $CONH_2$, CONH$C_1$–$C_6$) alkyl, CON[($C_1$–$C_6$) alkyl]$_2$, ($C_1$–$C_6$)-alkyl, ($C_2$–$C_6$)-alkenyl, ($C_2$–$C_6$)-alkynyl, O—($C_1$–$C_6$)-alkyl (where one, more than one or all hydrogen(s) in the alkyl, alkenyl and alkynyl radicals may be replaced by fluorine, or one hydrogen may be replaced by OH, $OC(O)CH_3$, $OC(O)H$, O—$CH_2$—Ph, $NH_2$, NH—CO—$CH_3$ or $N(COOCH_2Ph)_2$), $SO_2$—$NH_2$, $SO_2NH(C_1$–$C_6)$-alkyl, $SO_2N[(C_1$–$C_6)$-alkyl]$_2$, S—($C_1$–$C_6$)-alkyl, S—($CH_2$)$_n$-phenyl, SO—($C_1$–$C_6$)-alkyl, SO—($CH_2$)$_n$-phenyl, $SO_2$—($C_1$–$C_6$)-alkyl, $SO_2$—($CH_2$)$_n$-phenyl (where n is 0–6 and the phenyl radical may be substituted up to two times by F, Cl, Br, OH, $CF_3$, $NO_2$, CN, $OCF_3$, O—($C_1$–$C_6$)-alkyl, ($C_1$–$C_6$)-alkyl or $NH_2$), phenyl or O-phenyl (wherein the phenyl radical may be optionally substituted up to two times by F, Cl, Br, I, OH, $CF_3$, $NO_2$, CN, $OCF_3$, O—($C_1$–$C_6$)-alkyl, ($C_1$–$C_6$)-alkyl, $NH_2$, NH($C_1$–$C_6$)-alkyl, N(($C_1$–$C_6$)-alkyl)$_2$, $SO_2$—$CH_3$, COOH, COO—($C_1$–$C_6$)-alkyl or $CONH_2$);
R1 is H, F, Cl, Br, I, $CF_3$, CN, $NO_2$, COOH, COO($C_1$–$C_6$) alkyl, $CONH_2$, CONH($C_1$–$C_6$)alkyl, CON[($C_1$–$C_6$) alkyl]$_2$, ($C_1$–$C_6$)-alkyl, ($C_2$–$C_6$)-alkenyl, ($C_2$–$C_6$)-alkynyl, O—($C_1$–$C_6$)-alkyl (where one, more than one or all hydrogen(s) in the alkyl, alkenyl and alkynyl radicals may be replaced by fluorine, or one hydrogen may be replaced by OH, $OC(O)CH_3$, $OC(O)H$, O—$CH_2$—Ph, $NH_2$, NH—CO—$CH_3$ or $N(COOCH_2Ph)_2$), $SO_2$—$NH_2$, $SO_2NH(C_1$–$C_6$) =alkyl, $SO_2N[(C_1$–$C_6)$-alkyl]$_2$, S—($C_1$–$C_6$)-alkyl, S—($CH_2$)$_n$-phenyl, SO—($C_1$–$C_6$)-alkyl, SO—($CH_2$)$_n$-phenyl, $SO_2$—($C_1$–$C$)-alkyl, $SO_2$—$(CHO_2)_n$-phenyl (where n is 0–6 and the phenyl radical may be substituted up to two times by F, Cl, Br, OH, $CF_3$, $NO_2$, CN, $OCF_3$, O—($C_1$–$C_6$)-alkyl, ($C_1$–$C_6$)-alkyl or $NH_2$), phenyl or O-phenyl (wherein the phenyl radical may be optionally substituted up to two times by F, Cl, Br, I, OH, $CF_3$, $NO_2$, CN, $OCF_3$, O—$(C_1-C_6)$-alkyl, $(C_1-C_6)$-alkyl, $NH_2$, $NH(C_1-C_6)$-alkyl, $N((C_1-C_6)$-alkyl$)_2$, $SO_2$—$CH_3$, COOH, COO—$(C_1-C_6)$-alkyl or $CONH_2$);

R2 $NH_2$, NHR3 or NR4R5, wherein
  R3 is $(C_1-C_6)$alkyl, CN, CHO, CO—$NH_2$, CH=NH, C(S)—$NH_2$, C(=NH)—NH—phenyl (wherein the phenyl ring may be optionally substituted up to two times by F, Cl, Br, I, OH, $CF_3$, $NO_2$, CN, $OCF_3$, O—$(C_1-C_6)$-alkyl, $(C_1-C_6)$-alkyl, $NH_2$, $NH(C_1-C_6)$-alkyl, $N((C_1-C_6)$-alkyl$)_2$, $SO_2$—$CH_3$, COOH, COO—$(C_1-C_6)$-alkyl or $CONH_2$), phenyl or $CH_2$-phenyl (wherein the phenyl ring may be optionally substituted once to 3 times by F, Cl, Br, I, OH, $NO_2$, CN, $OCF_3$, O—$(C_2-C_6)$-alkyl, $(C_2-C_6)$-alkyl, $NH_2$, $NH(C_1-C_6)$-alkyl, $N((C_1-C_6)$-alkyl$)_2$, $SO_2$—$CH_3$, COOH, COO—$(C_1-C_6)$-alkyl or $CONH_2$);
  R4 is $C_1-C_6$-alkyl, $C_3-C_6$-cycloalkyl, $C_2-C_6$-alkenyl, $C_3-C_6$-alkynyl, phenyl or $CH_2$-phenyl (wherein the phenyl ring may be optionally substituted once or twice by F, Cl, Br, I, OH, $CF_3$, $NO_2$, CN, $OCF_3$, O—$(C_1-C_6)$-alkyl), $(C_1-C_6)$-alkyl, $NH_2$, $NH(C_1-C_6)$-alkyl, $N((c_1-C_6)$-alkyl$)_2$ $SO_2$—$CH_3$, COOH, COO—$(C_1-C_6)$-alkyl or $CONH_2$);
  R5 is $C_1-C_6$-alkyl, $C_3-C_6$-cycloalkyl, $C_2-C_6$-alkenyl, $C_3-C_6$-alkynyl, phenyl or $CH_2$-phenyl (wherein the phenyl ring may be optionally substituted once or twice by F, Cl, Br, I, OH, $CF_3$, $NO_2$ CN, $OCF_3$, O—$(C_1-C_6)$-alkyl$)_2$, $SO_2$—$CH_3$, COOH, COO—$(C_1-C_6)$-alkyl or $CONH_2$); or
  R4 and R5 together form one of the groups $CH_2$—$CH_2$—$CH_2$—$CH_2$, $CH_2$, $CH_2$—$CH_2$—$N(CH_2$-phenyl)—$CH_2$—$CH_2$, $CH_2$—$CH_2$—O—$CH_2$—$CH_2$ or $CH_2$—$CH_2$—$CH_2$—$CH_2$;

and their physiologically tolerated salts and physiologically functional derivatives.

A particularly preferred embodiment encompasses treating obesity with a pharmaceutical composition comprising a compound of formula I wherein:

Y is a direct linkage;
x is $CH_2$;
R1 is F, Cl, Br, I, $CF_3$, CN, $(C_1-C_6)$-alkyl, O—$(C_1-C_6)$-alkyl (where one, more than one or all hydrogen(s) in the alkyl radicals may be replaced by fluorine), $SO_2$—$NH_2$, $SO_2NH(C_1-C_6)$-alkyl, $SO_2N[(C_1-C_6)$-alkyl]$_2$, $SO_2$—$(C_1-C_6)$-alkyl, $SO_2$—$(CH_2)_n$-phenyl (where n is 0–6 and the phenyl radical may be substituted up to two times by F, Cl, Br, OH, $CF_3$, $NO_2$, CN, $OCF_3$, O—$(C_1-C_6)$-alkyl, $(C_1-C_6)$-alkyl or $NH_2$), phenyl, O-phenyl (wherein the phenyl radical may be optionally substituted up to two times by F, Cl, Br, OH, $CF_3$, $NO_2$, CN, $OCF_3$, O—$(C_1-C_6)$-alkyl or $(C_1-C_6)$-alkyl), or pyridyl;
R1' is H, F, Cl, Br, $CF_3$, CN, $(C_1-C_6)$-alkyl, O—$(C_1-C_6)$-alkyl (where one, more than one or all hydrogen(s) in the alkyl radicals may be replaced by fluorine), $SO_2$—$NH_2$, $SO_2NH(C_1-C_6)$-alkyl, $SO_2N[(C_1-C_6)$-alkyl]$_2$, $SO_2$—$(C_1-C_6)$-alkyl, $SO_2$—$(CH_2)_n$-phenyl (where n is 0–6 and the phenyl radical may be substituted up to two times by F, Cl, Br, OH, $CF_3$, $NO_2$, CN, $OCF_3$, O—$(C_1-C_6)$-alkyl, $(C_1-C_6)$-alkyl or $NH_2$), phenyl (wherein the phenyl radical may be optionally substituted up to two times by F, Cl, Br, OH, $CF_3$, $NO_2$, CN, $OCF_3$, O—$(C_1-C_6)$-alkyl or $(C_1-C_6)$-alkyl), or pyridyl;
R2 is $NH_2$, NHR3 or NR4R5, wherein
  R3 is $(C_1-C_6)$-alkyl, CN, CHO, CO—$NH_2$, CH=NH, C(S)—$NH_2$ or C(=NH)—NH—phenyl (wherein the phenyl ring may be optionally substituted up to two times by F, Cl, Br, OH, $CF_3$, $NO_2$, CN, $OCF_3$, O—$(C_1-C_6)$-alkyl, $NH_2$, $NH(C_1-C_6)$-alkyl or $N((C_1-C_6)$-alkyl$)_2$);
  R4 is $C_1-C_6$-alkyl;
  R5 is $C_1-C_6$-alkyl; or
  R4 and R5 together form a $CH_2$—$CH_2$—$CH_2$—$CH_2$—$CH_2$— group;

and their physiologically tolerated salts.

The method of treatment contemplated encompasses not only treatment by administration of a pharmaceutical composition which comprises a compound of formula (I) and a pharmaceutically acceptable carrier but also administration of the compound of formula (I) absent a pharmaceutically acceptable carrier.

The invention also relates to the use of compounds of the formula I in the form of their racemates, racemic mixtures and pure enantiomers, and to their diastereomers and mixtures thereof.

The alkyl, alkenyl and alkynyl radicals in the substituents R1, R1', R2, R3, R4, R5 and R6 may be either straight-chain or branched.

Pharmaceutically acceptable salts are particularly suitable for medical applications because of their greater solubility in water compared with the initial compounds on which they are based. These salts must have a pharmaceutically acceptable anion or cation. Suitable pharmaceutically acceptable acid addition salts of the compounds of the formula I are salts of inorganic acids such as hydrochloric acid, hydrobromic acid, phosphoric, metaphosphoric, nitric and sulfuric acids, and organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic, tartaric and trifluoroacetic acids. It is particularly preferred to use the chloride for medical purposes. Suitable pharmaceutically acceptable basic salts are ammonium salts, alkali metal salts (such as sodium and potassium salts) and alkaline earth metal salts (such as magnesium and calcium salts).

Salts with a pharmaceutically unacceptable anion likewise fall within the scope of the invention as useful intermediates for preparing or purifying pharmaceutically acceptable salts and/or for use in non-therapeutic, for example in vitro, applications.

The term "physiologically functional derivative" used herein refers to any physiologically tolerated derivative of a compound according to the invention, for example an ester, which is able on administration to a mammal, such as, for example, to humans, to form (directly or indirectly) such a compound or an active metabolite thereof.

A further aspect of this invention is the use of prodrugs of compounds of the formula I. Such prodrugs may be metabolized in vivo to a compound of the formula I. These prodrugs may themselves be active or not.

The compounds of the formula I may also exist in various polymorphous forms, for example as amorphous and crystalline polymorphous forms. All polymorphous forms of the compounds of the formula I fall within the scope of the invention and are a further aspect of the invention.

All references hereinafter to "compound(s) of the formula (I)" refer to compound(s) of the formula (I) as described above and to the salts, solvates and physiologically functional derivatives thereof as described herein.

The compounds of formula (I) are used in the treatment of obesity. Treatment of obesity encompasses prophylaxis and amelioration of obesity. The treatment regiment involves administering an obesity treating effective amount of a compound of formula (I) as part of a pharmaceutical composition.

The amount of a compound of the formula (I), which is an "effective amount," that is necessary to achieve the desired biological effect depends on a number of factors, for example the specific compound chosen, the intended use, the mode of administration and the clinical condition of the patient. The daily dose is generally in the range from 0.3 mg to 100 mg (typically from 3 mg to 50 mg) per day and per kilogram body weight, for example 3–10 mg/kg/day. An intravenous dose may be, for example, in the range from 0.3 mg to 1.0 mg/kg, which may suitably be administered as infusion of 10 ng to 100 ng per kilogram and per minute. Infusion solutions suitable for these purposes may contain, for example, from 0.1 ng to 10 mg, typically from 1 ng to 10 mg, per milliliter. Single doses may contain, for example, from 1 mg to 10 g of the active ingredient. Thus, ampoules for injections may contain, for example, from 1 mg to 100 mg, and single dose formulations which may be administered orally, such as, for example, tablets or capsules, may contain, for example, from 1.0 to 1000 mg, typically from 10 to 600 mg. In the case of pharmaceutically acceptable salts, the above weight data are based on the weight of the aminothiazole ion derived from the salt. The compounds of the formula (I) may be used for prophylaxis or therapy of the abovementioned states themselves as compound, but they are preferably in the form of a pharmaceutical composition with a compatible carrier. The carrier must, of course, be compatible in the sense of compatibility with other ingredients of the composition and not be harmful to the patient's health. The carrier may be a solid or a liquid or both and is preferably formulated with the compound as single dose, for example as tablet, which may contain from 0.05% to 95% by weight of the active ingredient. Further pharmaceutically active substances may likewise be present, including further compounds of the formula (I). The pharmaceutical compositions according to the invention may be produced by one of the known pharmaceutical methods which essentially consists of mixing the ingredients with pharmacologically acceptable carriers and/or excipients.

Pharmaceutical compositions according to the invention are those suitable for oral, rectal, topical, peroral (for example sublingual) and parenteral (for example subcutaneous, intramuscular, intradermal or intravenous) administration, although the most suitable mode of administration depends in each individual case on the nature and severity of the condition to be treated and on the nature of the compound of the formula (I) used in each case. Coated formulations and coated slow-release formulations also fall within the scope of the invention. Acid- and gastric fluid-resistant formulations are preferred. Suitable gastric fluid-resistant coatings comprise cellulose acetate phthalate, polyvinyl acetate phthalate, hydroxypropylmethylcellulose phthalate and anionic polymers of methacrylic acid and methyl methacrylate.

The pharmaceutical composition in the inventive method when in the form of a soft gelatin capsule may comprise about 100 mg of a compound of formula (I). The pharmaceutical composition in the inventive method when in the form of an emulsion may comprise about 60 mg of a compound of formula (I). The pharmaceutical composition in the inventive method when in the form of a rectal suppository may comprise about 40 mg of a compound of formula (I). The pharmaceutical composition in the inventive method when in the form of a tablet may comprise about 40 mg of a compound of formula (I). The pharmaceutical composition in the inventive method when in the form of a coated tablet may comprise about 50 mg of a compound of formula (I). The pharmaceutical composition in the inventive method when in the form of a hard gelatin capsule may comprise about 100 mg or about 140 mg of a compound of formula (I). The pharmaceutical composition in the inventive method when in the form of liquid drops may comprise about 100 mg of a compound of formula (I) in 1 ml of drops.

Suitable pharmaceutical compounds for oral administration may be in the form of separate units such as, for example, capsules, cachets, pastilles or tablets, each of which contains a defined amount of the compound of the formula (I); as powder or granules; as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. In general, the compositions are produced by uniform and homogeneous mixing of the active ingredient with a liquid and/or finely dispersed solid carrier, after which the product is shaped if necessary. Thus, for example, a tablet may be produced by compressing or shaping the powder or granules of the compound, where appropriate with one or more additional ingredients. Compressed tablets may be produced by tabletting the compound in free-flowing form, such as, for example, a powder or granules, where appropriate mixed with a binder, lubricant, inert diluent and/or one (or more) surface-active/dispersing agents in a suitable machine. Shaped tablets may be produced by shaping, in a suitable machine, the compound which is in powder form and has been moistened with an inert liquid diluent.

Pharmaceutical compositions suitable for peroral (sublingual) administration comprise suckable tablets which contain a compound of the formula (I) with a flavoring, normally sucrose, and gum arabic or tragacanth, and pastilles which contain the compound in an inert base such as gelatin and glycerol or sucrose and gum arabic.

Suitable pharmaceutical compositions for parenteral administration comprise preferably sterile aqueous preparations of a compound of the formula (I), which are preferably isotonic with the blood of the intended recipient. These preparations are preferably administered intravenously, although administration may also take place by subcutaneous, intramuscular or intradermal injection. These preparations may preferably be produced by mixing the compound with water and making the resulting solution sterile and isotonic with blood. Injectable compositions according to the invention generally contain from 0.1 to 5% by weight of the active compound.

Suitable pharmaceutical compositions for rectal administration are preferably in the form of single-dose suppositories. These may be produced by mixing a compound of the formula (I) with one or more conventional solid carriers, for example cocoa butter, and shaping the resulting mixture.

Suitable pharmaceutical compositions for topical use on the skin are preferably in the form of an ointment, cream, lotion, paste, spray, aerosol or oil. Carriers which may be used are petrolatum, lanolin, polyethylene glycols, alcohols and combinations of two or more of these substances. The active ingredient is generally present in a concentration of from 0.1 to 15% by weight of the composition, for example from 0.5 to 2%.

Transdermal administration is also possible. Suitable pharmaceutical compositions for transdermal applications may be in the form of single plasters which are suitable for long-term close contact with the patient's epidermis. Plasters of this type suitably contain the active ingredient in an aqueous solution which is buffered where appropriate, dissolved and/or dispersed in an adhesive or dispersed in a polymer. A suitable active ingredient concentration is about 1% to 35%, preferably about 3% to 15%. As a particular option, the active ingredient may be released by electrotransport or iontophoresis as described, for example, in Pharmaceutical Research, 2 (6): 318 (1986).

The following preparations serve to illustrate the invention without, however, restricting it.

EXAMPLE A

Soft gelatin capsules containing 100 mg of active ingredient per capsule:

|  | per capsule |
| --- | --- |
| active ingredient | 100 mg |
| triglyceride mixture fractrionated from coconut oil | 400 mg |
| capsule contents | 500 mg |

EXAMPLE B

Emulsion containing 60 mg of active ingredient per ml:

|  | per 100 ml of emulsion |
| --- | --- |
| active ingredient | 1.2 g |
| neutral oil | q.s. |
| sodium carboxymethylcellulose | 0.6 g |
| polyoxyethylene stearate | q.s. |
| glycerol, pure | 0.2 to 2.0 g |
| flavoring | q.s. |
| water (deionized or distilled) | ad 100 ml |

EXAMPLE C

Rectal drug form containing 40 mg of active ingredient per suppository;

|  | per suppository |
| --- | --- |
| active ingredient | 40 mg |
| suppository base | ad 2 g |

EXAMPLE D

Tablets containing 40 mg of active ingredient per tablet:

|  | per tablet |
| --- | --- |
| active ingredient | 40 mg |
| lactose | 600 mg |
| corn starch | 300 mg |
| soluble starch | 20 mg |
| magnesium stearate | 40 mg |
|  | 1000 mg |

EXAMPLE E

Coated tablets containing 50 mg of active ingredient per tablet:

|  | per tablet |
| --- | --- |
| active ingredient | 50 mg |
| corn starch | 100 mg |
| lactose | 60 mg |
| sec. calcium phosphate | 30 mg |
| soluble starch | 5 mg |
| magnesium stearate | 10 mg |
| colloidal silica | 5 mg |
|  | 260 mg |

EXAMPLE F

The following formulas are suitable for producing the contents of hard gelatin capsules:

| a) | active ingredient | 100 mg |
| --- | --- | --- |
|  | corn starch | 300 mg |
|  |  | 400 mg |
| b) | active ingredient | 140 mg |
|  | lactose | 180 mg |
|  | corn starch | 180 mg |
|  |  | 500 mg |

EXAMPLE G

Drops may be produced in accordance with the following formula (100 mg of active ingredient in 1 ml≘ 20 drops):

| active ingredient | 10 g |
| --- | --- |
| methyl benzoate | 0.07 g |
| ethyl benzoate | 0.03 g |
| ethanol, 96% | 5 ml |
| demineralized water | ad 100 ml |

The invention further relates to a process for preparing the compounds of general formula I, which comprises preparing compounds of the general formula I in accordance with the following reaction scheme:

Reaction scheme 1

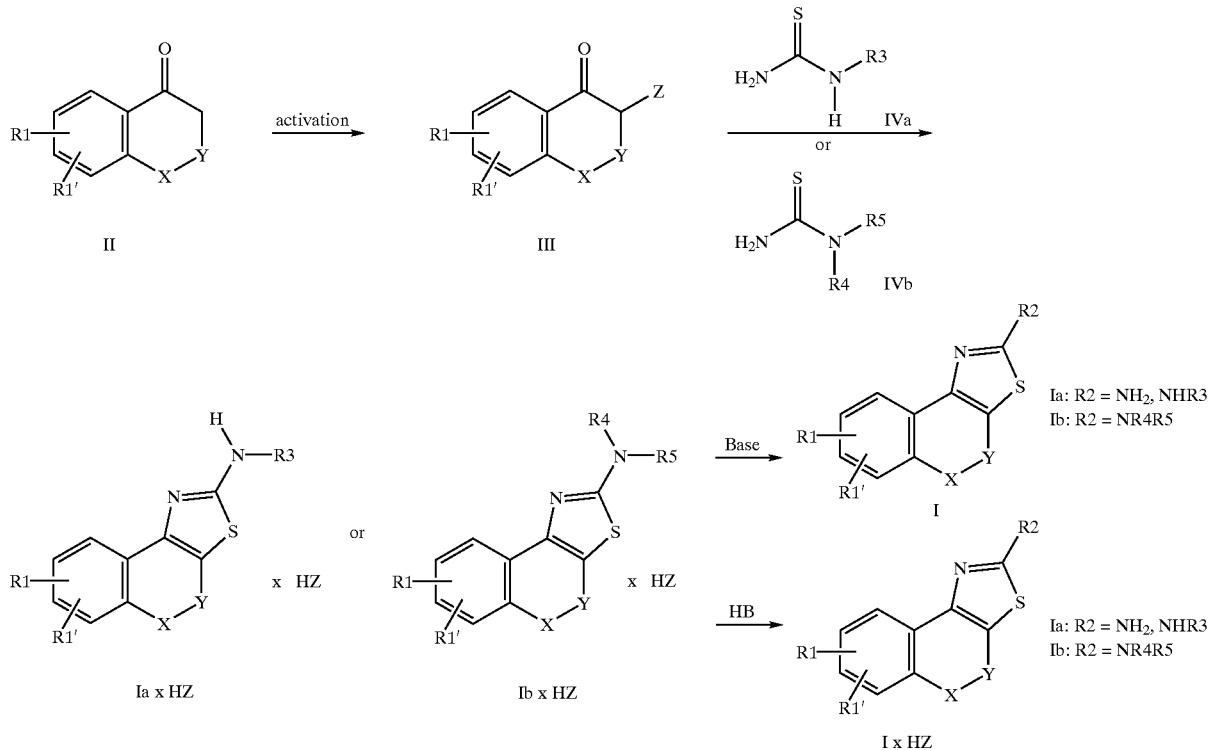

Bicyclic ketones of the general formula II in which R1, R1', X and Y have the stated meanings either are commercially available or may be prepared by methods known from the literature.

Bicyclic ketones of the formula H in which R1 or R1' are aryl radicals may be obtained by Pd(0)-catalyzed addition of boronic esters onto compounds of the formula II in which R1 and/or R1' are bromine, iodine or trifluoromethylsulfonyloxy (for example: N. Miyaura and A. Suzuki, Chem. Rev. 95, 2457–83 (1995) or T. Oh-e, N. Miyaura and A. Suzuki, J. Org. Chem. 58, 2201–08 (1993)).

Bicyclic ketones of the general formula II in which R1 and/or R1' are alkynyl radicals or alkenyl radicals may be prepared, for example, by methods like those described by K. Sonagashira et al., Tetrahedron Lett. 4467 (1975) and S. Takahashi et al., Synthesis 627 (1980) (palladium-catalyzed reaction of, for example, trimethylsilylacetylene or alkynes) or by E. Negishi et al., J. Org. Chem. 62, 8957–60 (1997) (alkynylzinc bromide) or by A. Hassner et al., J. Org. Chem. 49, 2546 (1984) (trialkylstannylalkynes, trialkylstannylvinyl or allyl compounds, 1-alkenylboron compounds or vinyl compounds).

The bicyclic ketones of the general formula II are activated most simply by a reaction with bromine to give the alpha-bromo ketone of the general formula III (Z=Br). Z in the activated compounds of the general formula III may, however, also advantageously be Cl, I, O—C(O)—$C_6H_4$—4—$NO_2$, O—$SO_2$—$CH_3$, O—$SO_2$—$CF_3$, O—$SO_2$—$C_6H_4$—4—$CH_3$ or O—$SO_2$—$C_6H_5$.

Compounds of the general formula I×HZ are obtained by reacting thioureas of the general formula IVa or IVb in which R2=$NH_2$, NHR3 or R2=NR4R5, and the radicals R2, R3, R4 and R5 have the stated meanings. The procedure for this is advantageously such that the compounds III are reacted with the thioureas IVa or IVb in the molar ratio of from 1:1 to 1:1.5. The reaction is advantageously carried out in an inert solvent, for example in polar organic solvents such as dimethylformamide, dimethylacetamide, N-methyl-2-pyrrolidone, dimethyl sulfoxide, dioxane, tetrahydrofuran, acetonitrile, nitromethane or diethylene glycol dimethyl ether. However, solvents which prove to be particularly advantageous are methyl acetate and ethyl acetate, short-chain alcohols such as methanol, ethanol, propanol, isopropanol, and lower dialkyl ketones such as, for example, acetone, 2-butanone or 2-hexanone. It is also possible to use mixtures of the reaction media mentioned; thus, it is also possible to use mixtures of the solvents mentioned with solvents which are less suitable on their own, such as, for example, mixtures of methanol with benzene, ethanol with toluene, methanol with diethyl ether or with tert-butyl methyl ether, ethanol with tetrachloromethane, acetone with chloroform, dichloromethane or 1,2-dichloroethane, it being expedient for the more polar solvent in each case to be used in excess. The reactants may be present either in suspension or solution in the particular reaction medium. It is also possible in principle for the reactants to be reacted without a solvent, especially when the particular thioamide has a low melting point. The reaction is only slightly exothermic and may be carried out at between −10° C. and 150° C., preferably between 50° C. and 100° C. A temperature range between 50° C. and 80° C. usually proves to be particularly favorable.

The reaction time depends substantially on the reaction temperature and is between 2 minutes and 3 days at higher and lower temperatures respectively. In the favorable temperature range, the reaction time is generally between 5 minutes and 48 hours.

The resulting salts of the compounds of the general formula Ia×HZ and Ib×HZ may be converted with organic or inorganic bases into the free basic compounds of the formula I (Ia: R2=NH$_2$, NHR3; Ib: R2=NR4R5). The compounds of the general formula I may be converted into their acid addition salts of the general formula I×HB by reaction with organic or inorganic acids of the formula HB. Examples of suitable inorganic acids HB are: hydrohalic acids such as hydrochloric acid and hydrobromic acid, and sulfuric acid, phosphoric acid and sulfamic acid. Examples of organic acids HB which may be mentioned are: formic acid, acetic acid, benzoic acid, ptoluenesulfonic acid, benzenesulfonic acid, succinic acid, fumaric acid, maleic acid, lactic acid, tartaric acid, citric acid, L-ascorbic acid, salicylic acid, isethionic acid, methanesulfonic acid, trifluoromethane-sulfonic acid, 1,2-benzisothiazol-3(2H)-one, 6-methyl-1,2,3-oxathiazin-4(3H)-one 2,2-dioxide.

Apart from the derivatives described in the examples, also obtained according to the invention are the compounds of the general formula I, and their acid addition products, compiled in the following tables:

The compounds of the formula I are distinguished by beneficial effects on lipid metabolism, and they are particularly suitable as anorectic agents. The compounds may be employed alone or in combination with other anorectic active ingredients. Further anorectic active ingredients of this type are mentioned, for example, in the Rote Liste, chapter 01 under weight-reducing agents/appetite suppressants. Examples include, but are not limited to, Decorpa© (from Pierre Fabre Pharma, common name, sterculia), Xenical© (from Roche, common name orlistat), Antiadipositum X-112S (from Haenseler, common name, D-norpseudoephedrin-HCl), Fasupond© (from Eu Rho Arzneil, common name, D-norpseudoephedrin-HCl), Mirapront© N (from Mack, Illert., common name, D-norpseudoephedrin-Poly(styrol, divinylbenzol) sulfonate), Regenon© l-retard (from Temmler Pharma, common name, Amfepramon-HCl), Rondimen© (from ASTA Medica AWD, common name, Mefenorex-HCl), Tenuate© Retard (from Artegodan, common name, Amfepramon-HCl), Vita-Schlanktropfen Schuck (from Schuck, common name, D-norpseudoephedrin-HCl), Vencipon© N (from Artesan, common name, Ephedrin-HCl), Cefamadar© (from

TABLE 1

Examples

Formula I

| Example | R$_1$; R$_1$' | R$_2$ | Y | X | Salt | m.p.[° C.] |
|---|---|---|---|---|---|---|
| 1 | 6-Cl; H | N(CH$_3$)$_2$ | — | CH$_2$ | HBr | 298 |
| 2 | 6-CN; H | N(CH$_3$)$_2$ | — | CH$_2$ | HBr | >300 |
| 3 | 6-Cl; H | NH—C(S)—NH$_2$ | — | CH$_2$ | — | 215 |
| 4 | 6-Cl; H | NH—CN | — | CH$_2$ | — | 225 |
| 5 | 6-Cl; H | N(CH$_3$)$_2$ | — | CH$_2$ | HCl | 219 |
| 6 | 6-Cl; H | NH—CHO | — | CH$_2$ | — | 295 |
| 7 | 6-Cl; H | NH—C(=NH)—NH—C$_6$H$_5$ | — | CH$_2$ | — | 210 |
| 8 | 6-Cl; H | NH—(C=NH)—NH—C$_6$H$_4$-4-Cl | — | CH$_2$ | — | 195 |
| 9 | 6-Cl; H | NH—C(O)CH$_3$ | — | CH$_2$ | — | 305 |
| 10 | 6-Cl; H | NH—CO—NH$_2$ | | CH$_2$ | HBr | 295 |
| 11 | 5-SO$_2$—NH$_2$; 6-Cl | NH$_2$ | — | CH$_2$ | HBr | 305 |
| 12 | 5-Cl; H | NH(CH$_3$) | CH$_2$ | O | HCl | 196 |
| 13 | 5-SO$_2$—CH$_3$; H | NH$_2$ | — | CH$_2$ | HCl | >230 |
| 14 | 5-SO$_2$—CH$_3$; H | NH(CH$_3$) | — | CH$_2$ | HCl | >230 |
| 15 | 5-SO$_2$—CH$_3$; 6 Cl | NH$_2$ | — | CH$_2$ | HCl | >250 |
| 16 | 6-(C$_6$H$_4$-4-OCH$_3$); H | NH(CH$_3$) | — | CH$_2$ | — | 190 |
| 17 | 6-(OC$_6$H$_4$-4-Cl); H | NH(CH$_3$) | — | CH$_2$ | HCl | 241 |
| 18 | 6-O—CH$_2$—CF$_2$—CF$_3$H | NH(CH$_3$) | — | CH$_2$ | HCl | 258 |
| 19 | 6-O—CH$_2$—CF$_3$; H | NH(CH$_3$) | — | CH$_2$ | HCl | 242 |
| 20 | 6-O—CH$_2$—CF$_3$; H | NH$_2$ | — | CH$_2$ | HCl | 235 |
| 21 | 6-O—CH$_2$—CF$_2$—CF$_3$; H | NH$_2$ | — | CH$_2$ | HCl | 216 |
| 22 | 7-(C$_6$H$_4$-4-CF$_3$); H | NH(CH$_3$) | — | CH$_2$ | — | 221 |
| 23 | 7-(C$_6$H$_4$-4-CF$_3$); H | NH$_2$ | — | CH$_2$ | — | 227 |
| 24 | 5-(C$_6$H$_4$-4-Cl); H | N(CH$_3$)$_2$ | — | CH$_2$ | HOAc | 260 |
| 25 | 5-(C$_6$H$_4$-4-CF$_3$); H | NH$_2$ | — | CH$_2$ | HBr | 232 |
| 26 | 6-(pyrid-3-yl); H | NH(CH$_3$) | — | CH$_2$ | HCl | 225 |
| 27 | 6-(OC$_6$H$_4$-3-CH$_3$); H | NH$_2$ | — | CH$_2$ | HCl | 174 |
| 28 | 6-(OC$_6$H$_4$-3-CH$_3$); H | NH(CH$_3$) | — | CH$_2$ | HCl | 178 |
| 29 | 6-(OC$_6$H$_5$); H | NH$_2$ | — | CH$_2$ | HCl | 148 |
| 30 | 6-O—CH$_2$CF$_2$—CF$_2$—CF$_3$; H | NH(CH$_3$) | — | CH$_2$ | HCl | 237 |
| 31 | 5-(C$_6$H$_4$—Cl); H | N(CH$_3$)$_2$ | — | CH$_2$ | HBR | 254 |
| 32 | 6-O—C$_6$H$_4$-4-Cl; H | NH$_2$ | — | CH$_2$ | HCl | 216 |
| 33 | 6-Cl; H | piperidin-1-yl | — | CH$_2$ | — | 95 |

Cefak, common name Madar D4), and Helianthus tuberosus (Plantina). The compounds are suitable for the prophylaxis and, in particular, for the treatment of obesity.

The activity of the compounds has been tested as follows:
Biological Test Model

The anorectic effect was tested on male NMRI mice. After withdrawal of feed for 24 hours, the test product was administered by gavage. The animals were housed singly and had free access to drinking water and, 30 minutes after administration of the product, they were offered condensed milk. The consumption of condensed milk was determined, and the general behavior of the animals was inspected, every half hour for 7 hours. The measured milk consumption was compared with that of untreated control animals.

of 48% strength HBr solution in water and affords 2-bromo-1-oxoindane-5-carbonitrile with a melting point of 115–118° C.

c) 2-Dimethylamino-8H-indeno[1,2-d]thiazole-6-carbonitrile hydrobromide:

236 mg of 2-bromo-1-oxoindane-5-carbonitrile are heated under reflux with 156 mg of NN-dimethylthiourea in 10 ml of triacetone for 3 h. The reaction mixture is concentrated in vacuo; the residue is stirred with a little acetone, filtered off with suction, washed with acetone and dried in vacuo. 2-Dimethylamino-8H-indeno[1,2-d]thiazole-6-carbonitrile hydrobromide is obtained with a melting point>300° C.

TABLE 2

Anorectic effect measured by reduction in the cumulative milk consumption by treated animals compared with untreated animals.

| Compound/Example Formula I | Oral dose [mg/kg] | Number of animals/cumulative milk consumption by the treated animals N/[ml] | Number of animals/ cumulative milk consumption by the untreated control animals N/[ml] | Reduction in the cumulative milk consumption as % of the controls |
|---|---|---|---|---|
| Example 1 | 50 | 12/1.76 | 12/4.05 | 56 |
| Example 2 | 50 | 5/0.76 | 5/5.14 | 85 |
| Example 6 | 50 | 5/0.96 | 5/4.20 | 77 |
| Example 18 | 50 | 5/0.38 | 5/3.84 | 90 |
| Example 19 | 50 | 5/0.28 | 5/3.82 | 93 |
| Example 20 | 50 | 5/0.46 | 5/3.82 | 88 |
| Example 26 | 50 | 5/0.68 | 5/2.94 | 77 |
| Example 27 | 50 | 5/0.74 | 5/3.54 | 79 |
| Example 30 | 50 | 5/0.14 | 5/3.58 | 96 |

The examples detailed below serve to illustrate the invention without, however, restricting it. The stated decomposition points are not corrected and generally depend on the heating rate.

PROCEDURE EXAMPLE 1

2-Dimethylamino-8H-indeno[1,2-d]thiazole-6-carbonitrile hydrobromide (Compound of Example 02):

a) 1-Oxoindane-5-carbonitrile:

9.5 g of 5-bromo-1-indanone and 4.93 g of CuCN are suspended in 10 ml of dimethylformamide and boiled under reflux for 4 hours. A solution of 18 g of iron(II) chloride in 5 ml of concentrated hydrochloric acid with 30 ml of water are added dropwise to the cooled, dark-brown viscous suspension while stirring, and the mixture is then stirred at 70° C. for 30 minutes. The reaction mixture is extracted by shaking three times with 50 ml of toluene, and the combined organic phases are extracted by shaking with 50 ml of 2N hydrochloric acid and 50 ml of 2N sodium hydroxide solution and then washed with water until neutral. The toluene extract is dried over magnesium sulfate and concentrated in vacuo, and the residue is recrystallized from n-heptane. 1-oxoindane-5-carbonitrile is obtained with a melting point of 123–125° C.

b) 2-Bromo-1-oxoindane-5-carbonitrile:

1-Oxoindane-5-carbonitrile is brominated with bromine in glacial acetic acid with addition of a catalytic amount

PROCEDURE EXAMPLE 2

N-(6-chloro-8H-indeno[1,2-d]thiazol-2-yl)formamide (compound of Example 6):

a) 2-Bromo-5-chloro-1-indanone:

Bromination of 5-chloro-1-indanone in glacial acetic acid with bromine and with addition of catalytic amounts of 48% strength HBr solution in water affords 2-bromo-5-chloro-1-indanone with a melting point of 94–96° C. A little of the corresponding dibromo compound is obtained as byproduct.

b) 6-Chloro-8H-indeno[1,2-d]thiazol-2-ylamine:

10 g of 2-bromo-5-chloro-1-indanone are dissolved in 300 ml of dry methanol at room temperature, and 4.6 g of thiourea are added. After stirring at room temperature for 5 hours, the solvent is removed in vacuo, and the residue is stirred in acetone, filtered off with suction, washed with acetone and dried in vacuo. A suspension of the salt in ethyl acetate is neutralized with triethylamine. The organic phase is washed twice with water and then twice with saturated brine, dried over magnesium sulfate, filtered and then concentrated in vacuo. 6-Chloro-BH-indeno[$_{1,2}$-d]thiazol-2-ylamine is obtained and is reacted further without further purification.

c) N-(6-Chloro-8H-indeno[$_{1,2}$-d]thiazol-2-yl)formamide:

1.1 g of the free base are stirred in a mixture of 19 ml of acetic anhydride and 7.5 ml of formic acid at 60° C. for 3 h. The reaction mixture is stirred at room temperature

PROCEDURE EXAMPLE 3

N-(6-Chloro-8H-indeno[1,2-d]thiazol-2-yl)-N'-phenylguanidine (compound of Example 7):

a) (6-Chloro-8H-indeno[1,2-d]thiazol-2-yl)thiourea hydrobromide:

10 g of 2-bromo-5-chloro-1-indanone are dissolved in 400 ml of dry ethanol at room temperature, and 11 g of dithiobiuret are added. After 5 h at room temperature, the yellow precipitate of the hydrobromide of (6-chloro-8H-indeno[1,2-d]thiazol-2-yl)-thiourea is filtered off with suction, washed with ethanol and dried and employed without purification in the next stage.

b) 6-Chloro-8H-indeno[1,2-d]thiazol-2-yl-cyanamide:

3.63 g of the above compound are dissolved in 500 ml of 2 N sodium hydroxide solution under reflux. 4.2 g of lead(II) acetate 3-hydrate, dissolved in 50 ml of water, are slowly added dropwise to this solution over the course of 20 mm. After one hour, the precipitate (lead sulfide) is filtered off with hot suction. The filtrate is acidified with glacial acetic acid, and the precipitate which has formed is filtered off with suction at 0° C. Further product is obtained by boiling the lead sulfide precipitate with methanol. 6-Chloro-8H-indeno[1,2-d]thiazol-2-yl-cyanamide is obtained with a melting point of 225° C.

c) N-(6-Chloro-8H-indeno[1,2-d]thiazol-2-yl)-N'-phenylguanidine:

0.26 g of 6-chloro-8H-indeno[1,2-d]thiazol-2-yl-cyanamide is suspended in 10 ml of ethanol at room temperature and, after addition of 0.1 of aniline, heated to reflux for 6 h. The reaction mixture is concentrated in vacuo, and the residue is purified by chromatography on silica gel with 5/1 dichloromethane/ethyl acetate. N-(6-Chloro-8H-indeno[1,2-d]thiazol-2-yl)-N'-phenylguanidine is obtained and melts with decomposition at 210° C.

PROCEDURE EXAMPLE 4

5-Methanesulfonyl-8H-indeno[1,2-d]thiazol-2-ylamine hydrochloride (compound of Example 13):

a) 2-Amino-5-methanesulfonyl-8,8a-dihydroindeno[1,2-d]thiazol-3a-ol hydrochloride:

2.3 g of 2-bromo-6-methanesulfonyl-1-indanone are dissolved in 50 ml of acetone and, while stirring, 0.67 g of thiourea is added. The solution is initially clear but, after a few minutes, the hydrobromide of the ring-closed compound crystallizes out. After stirring at room temperature for 4 h, the solid is filtered off with suction and dissolved in about 30 ml of methanol, and 1 ml of triethylamine is added. Once again, precipitation starts after a few minutes. After 15 min, 150 ml of water are added, and product formation is completed by stirring at room temperature. The precipitate is filtered off with suction, washed with water and dried in air. Dissolving in ethyl acetate, adding ethereal hydrochloric acid, filtering off the product which is formed with suction and drying in vacuo result in the hydrochloride of 2-amino-5-methanesulfonyl-8,8a-dihydroindeno[1,2-dithiazol-3a-ol with a decomposition point of 241° C.

b) 5-Methanesulfonyl-8H-indeno[1,2-d[thiazol-2-ylamine hydrochloride:

1 g of the compound obtained under a) is stirred in 100 ml of 50% concentrated hydrochloric acid at room temperature for 10 h, and the product is filtered off with suction and briefly washed with cold water. 5-Methanesulfonyl-8H-indeno[1,2-d]thiazol-2-ylamine hydrochloride of melting point 230° C. is obtained.

PROCEDURE EXAMPLE 5

6-Chloro-5-methanesulfonyl-8H-indeno[1,2-d]thiazol-2-ylamine hydrochloride (compound of Example 15):

6-Chloro-5-methanesulfonyl-8H-indeno[1,2-d]thiazol-2-ylamine hydrochloride, of melting point>260° C. is obtained in the manner described previously starting from 2-bromo-5-chloro-6-methanesulfonyl-1-indanone.

PROCEDURE EXAMPLE 6

Methyl[6-(2,2,3,3,3-pentafluoropropoxy)-8H-indeno[1,2-d]thiazol-2-yl]amine hydrochloride (compound of Example 18):

a) 5-(2,2,3,3,3-pentafluoropropoxy)-1-indanone:

6.5 g of 5-fluoro-1-indanone are dissolved in 50 ml of dry dimethylacetamide and, after addition of 36.5 g of anhydrous ground potassium carbonate and 12.9 g of 2,2,3,3,3-pentafluoropropanol, stirred at 95–100° C. for 10 h. The solvent is then removed by distillation in vacuo; 300 ml of water are added to the residue, and the aqueous phase is extracted with ethyl acetate several times. The organic phase is washed with water, dried over sodium sulfate and concentrated in vacuo. Purification on silica gel affords 5-(2,2,3,3,3-pentafluoropropoxy)-1-indanone as a brown oil which crystallizes after some time; melting point 52–54° C.

b) 2-Bromo-5-(2,2,3,3,3-pentafluoropropoxyl)-1-indanone:

6.9 g of 5-(2,2,3,3,3-pentafluoropropoxy)-1-indanone are dissolved in 100 ml of ethyl acetate, and a solution of 3.9 g of bromine in 15 ml of ethyl acetate is added dropwise. The solution is briefly heated to reflux before the remainder of the bromine solution is added dropwise. It is then stirred at room temperature for 2 h. The reaction solution is concentrated in vacuo and affords 2-bromo-5-(2,2,3,3,3-pentafluoropropoxy)-1-indanone as an oil which is employed without further purification in the next stage.

c) Methyl-[6-(2,2,3,3,3-pentafluoropropoxy)-8H-indeno[1,2-d]thiazol-2-yl]-amine hydrochloride:

1.79 g of 2-bromo-5-(2,2,3,3,3-pentafluoropropoxy)-1-indanone are dissolved in 60 ml of ethyl acetate, and a suspension of 450 mg of N-methylthiourea in 20 ml of ethyl acetate is added. The reaction solution is stirred at room temperature for 7 h; the pale precipitate is filtered off with suction and washed with ethyl acetate and then dried. The resulting hydrobromide is dissolved in 60 ml of methanol and, after addition of 1.53 g of triethylamine, stirred at room temperature for 5 h. The solution is concentrated; the residue crystallizes on addition of water. The dried free base is dissolved in ethyl acetate, and ethereal HCl solution is added until the reaction is acidic. After 3 h at room temperature, the crystals which are formed are filtered off with suction and dried in vacuo. To prepare the unsaturated system, the dried crystals are heated to reflux in 35 ml of glacial acetic acid for 2 h. The solvent is distilled off in vacuo and the solid residue is stirred with diisopropyl ether, filtered off with suction and dried in vacuo. Methyl[6-(2,2,3,3,3-pentafluoropropoxy)-8H-indeno[1,2-d]

thiazol-2-yl]amine hydrochloride is obtained with a melting point of 258° C.

PROCEDURE EXAMPLE 7
Methyl(6-pyridin-3-yl-8H-indeno[1,2-d]thiazol-2-yl)amine hydrochloride (compound of Example 26):

a) 5-pyridin-3-yl-1-indanone:

13.26 g of 3-bromopyridine are dissolved in 160 ml of diethyl ether and cooled to −60° C. To this solution are added dropwise over the course of 30 minutes 52 ml of a 1.6 molar solution of n-butyllithium in n-hexane. The solution is allowed to warm to −30° C. and, at this temperature, 9.5 ml of trimethyl borate are added dropwise with stirring. The reaction mixture is subsequently heated under reflux for 3 hours and then cooled to 0° C., and 6.1 ml of 1,3-propanediol are added dropwise. This mixture is stirred at 0° C. for 30 minutes before adding 5.46 ml of methanesulfonic acid dropwise and stirring for a further 30 minutes. Then 20 g of Celite are added, the mixture is warmed to room temperature and filtered, the filtrate is concentrated, the residue is stirred in 700 ml of toluene and, after renewed filtration, the solvent is removed by distillation in vacuo. 4.1 g of the residue (3[1,3,2] dioxaborinan-2-ylpyridine) are dissolved, without further purification, together with 4.22 g of 5-bromo-1-indanone and 4.24 g of sodium carbonate in a mixture of 100 ml of toluene with 20 ml of ethanol and 20 ml of water. The solution is degassed with argon and then 112 mg of palladium(II) acetate and 262 mg of triphenylphosphine are added. The reaction mixture is boiled under reflux for 4 hours and cooled to room temperature, and the ethanol content in the mixture is removed by distillation in vacuo. Then 50 ml of a 0.5 N sodium hydroxide solution are added with stirring, the organic phase is separated off and the aqueous phase is extracted by shaking with toluene. The combined organic phases are extracted by shaking successively with water and saturated brine, dried over magnesium sulfate, concentrated in vacuo and purified by chromatography on silica gel with 1/1 ethyl acetate/n-heptane. 5-Pyridin-3-yl-1-indanone is obtained with a melting point of 103–106° C.

b) 2-Chloro-5-pyridin-3-yl-1-indanone:

3.22 g of 5-pyridin-3-yl-1-indanone are dissolved in 160 ml of dichloromethane and, at 0° C., a solution of 1.34 ml of sulfuryl chloride in 40 ml of dichloromethane is added dropwise over the course of 15 minutes. After stirring at 0° C. for 30 minutes and then at room temperature for 60 minutes, 50 ml of a saturated sodium bicarbonate solution are slowly added. The organic phase is separated off, washed with water, dried over magnesium sulfate, concentrated in vacuo and purified by chromatography on silica gel with 50/1 dichloromethane/methanol. 2-Chloro-5-pyridin-3-yl-1-indanone with a melting point of 103–105° C. is obtained (in addition to 2,2-dichloro-5-pyridin-3-yl-1-indanone with a melting point of 109° C.).

c) Methyl-(6-pyridin-3-yl-8H-indeno[1,2-d]thiazol-2-yl) amine hydrochloride:

366 mg of 2-chloro-5-pyridin-3-yl-1-indanone are dissolved with 203 mg of N-methylthiourea in 5 ml of methanol and heated to reflux for 7 h. The reaction mixture is cooled and, after addition of 20 ml of acetone, the precipitate is filtered off with suction, washed with acetone and dried in vacuo. Methyl(6-pyridin-3-yl-8H-indeno[1,2-d]thiazol-2-yl)amine hydrochloride is obtained with a melting point of 225° C.

PROCEDURE EXAMPLE 8
6-m-Tolyloxy-8H-indeno[1,2-d]thiazol-2-yl-amine hydrochloride (compound of Example 27):

a) 5-m-Tolyloxy-1-indanone:

5 g of 5-fluoro-1-indanone are dissolved in 50 ml of dry dimethylformamide, and 18.2 g of anhydrous, powdered potassium carbonate and 3.57 g of m-cresol are added. The reaction mixture is stirred at 110° C. for 6 h. The solvent is removed by distillation in vacuo, and the residue is mixed with 100 ml of water and stirred for 2 h. The aqueous residue is extracted with ethyl acetate, and the organic extract is washed 3× with water, dried over sodium sulfate, filtered and concentrated in vacuo. 5-m-Tolyloxy-1-indanone is obtained as a brown oil which is reacted further without further purification.

b) 2-Bromo-5-m-tolyloxy-1-indanone:

Bromination of 5-m-tolyloxy-1-indanone takes place in analogy to the bromination of 5-(2,2,3,3,3-pentafluoropropoxy)-1-indanone (Example 6) and affords 2-bromo-5-m-tolyloxy-1-indanone as a pale brown oil.

c) 6-m-Tolyloxy-8H-indeno[1,2-d]thiazol-2-ylamine hydrochloride:

1.4 g of the above bromo ketone are dissolved in 14 ml of acetone and, after addition of 340 mg of thiourea in 20 ml of acetone, stirred at room temperature for 7 h. The crystals (2-amino-6-m-tolyloxy-8,8a-dihydroindeno[1,2-d]thiazol-3a-ol hydrobromide) which have separated out are filtered off with suction and dried in vacuo. As described in Example 6, this hydrobromide is also converted into the free base and further into the hydrochloride. The hydrochloride of 2-amino-6-m-tolyloxy-8,8a-dihydroindeno[1,2-d]thiazol-3a-ol is suspended in 30 ml of glacial acetic acid and heated to reflux with stirring. After 2 h, the solution is concentrated in vacuo, and the residue is stirred with diisopropyl ether, filtered off with suction and dried in vacuo. 6-m-Tolyloxy-8H-indeno[1,2-d]thiazol-2-ylamine hydrochloride is obtained with a melting point of 174° C.

What is claimed is:

1. A method for the treatment of obesity comprising administering to a patient in need thereof an obesity treating effective amount of a pharmaceutical composition comprising a compound of formula I

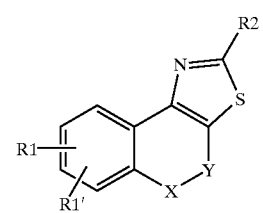

I in which

Y is a direct linkage, $CH_2$ or $CH_2—CH_2$;

X is $CH_2$, O, NH, NR6 or S;

R1, R1' are independently H, F, Cl, Br, I, $CF_3$, CN, $NO_2$, COOH, $COO(C_1–C_6)$alkyl, $CONH_2$, $CONH(C_1–C_6)$ alkyl, $CON((C_1–C_6)alkyl)_2$, $(C_1–C_6)$-alkyl, $(C_2–C_6)$-alkenyl, $(C_2–C_6)$-alkynyl, $O—(C_1–C_6)$-alkyl (wherein one, more than one or all hydrogen(s) in the alkyl, alkenyl and alkynyl radicals may be replaced by fluorine, or one hydrogen may be replaced by OH, OC(O)CH$_3$, OC(O)H, O—CH$_2$—Ph, NH$_2$, NH—CO—CH$_3$ or N(COOCH$_2$Ph)$_2$), SO$_2$—NH$_2$, SO$_2$NH(C$_1$–C$_6$)-alkyl, SO$_2$N((C$_1$–C$_6$)-alkyl)$_2$, S—(C$_1$–C$_6$)-alkyl, S—(CH$_2$)$_n$-phenyl, SO—(C$_1$–C$_6$)-alkyl, SO—(CH$_2$)$_n$-phenyl, SO$_2$—(C$_1$–C$_6$)-alkyl, SO$_2$—(CH$_2$)$_n$-phenyl (wherein n is 0–6 and the phenyl radical may be substituted up to two times by F, Cl, Br, OH, CF$_3$, NO$_2$, CN, OCF$_3$, O—(C$_1$–C$_6$)-alkyl, (C$_1$–C$_6$)-alkyl or NH$_2$), NH$_2$, NH—(C$_1$–C$_6$)-alkyl, N((C$_1$–C$_6$)-alkyl)$_2$, NH(C$_1$–C$_7$)-acyl, phenyl, biphenylyl, O—(CH$_2$)$_n$-phenyl (wherein n is 0–6), 1- or 2-naphthyl, 2-, 3- or 4-pyridyl, 2- or 3-furanyl, 2- or 3-thienyl (wherein the phenyl, biphenylyl, naphthyl, pyridyl, furanyl or thienyl rings may be optionally substituted up to 3 times by F, Cl, Br, I, OH, CF$_3$, NO$_2$, CN, OCF$_3$, O—(C$_1$–C$_6$)-alkyl, (C$_1$–C$_6$)-alkyl, NH$_2$, NH(C$_1$–C$_6$)-alkyl, N((C$_1$–C$_6$)-alkyl)$_2$, SO$_2$—CH$_3$, COOH, COO—(C$_1$–C$_6$)-alkyl or CONH$_2$), 1,2,3-triazol-5-yl (wherein the triazol ring may be optionally substituted in position 1, 2 or 3 by methyl or benzyl) or tetrazol-5-yl (wherein the tetrazol ring may be optionally substituted in position 1 or 2 by methyl or benzyl);

R2 is NH$_2$, NHR3 or NR4R5, wherein
R3 is (C$_1$–C$_6$)alkyl, CN, CHO, CO—NH$_2$, CH=NH, C(S)—NH$_2$, C(=NH)—NH-phenyl (wherein the phenyl ring may be optionally substituted up to two times by F, Cl, Br, I, OH, CF$_3$, NO$_2$, CN, OCF$_3$, O—(C$_1$–C$_6$)-alkyl, (C$_1$–C$_6$)-alkyl, NH$_2$, NH(C$_1$–C$_6$)-alkyl, N((C$_1$–C$_6$)-alkyl)$_2$, SO$_2$—CH$_3$, COOH, COO—(C$_1$–C$_6$)-alkyl or CONH$_2$), phenyl or CH$_2$-phenyl (wherein the phenyl ring may be optionally substituted up to 3 times by F, Cl, Br, I, OH, NO$_2$, CN, OCF$_3$, O—(C$_2$–C$_6$)-alkyl, (C$_2$–C$_6$)-alkyl, NH$_2$, NH(C$_1$–C$_6$)-alkyl, N((C$_1$–C$_6$)-alkyl)$_2$, SO$_2$—CH$_3$, COOH, COO—(C$_1$–C$_6$)-alkyl or CONH$_2$), biphenylyl, 1- or 2-naphthyl, 4-pyridyl, 2- or 3-furanyl, 2- or 3-thienyl, 5-tetrazolyl (wherein the biphenylyl, naphthyl, pyridyl, furanyl or thienyl rings may be optionally substituted up to two times by F, Cl, Br, I, OH, CF$_3$, NO$_2$, CN, OCF$_3$, O—(C$_1$–C$_6$)-alkyl, (C$_1$–C$_6$)-alkyl, NH$_2$, NH(C$_1$–C$_6$)-alkyl, N((C$_1$–C$_6$)-alkyl)$_2$, SO$_2$—CH$_3$, COOH, COO—(C$_1$–C$_6$)-alkyl or CONH$_2$), CH$_2$-phenyl, CH$_2$-2-pyridyl or CH$_2$-4-pyridyl (wherein the phenyl or pyridyl ring may be optionally substituted once or twice by F, Cl, Br, I, OH, CF$_3$, NO$_2$, CN, OCF$_3$, O—(C$_1$–C$_6$)-alkyl, (C$_1$–C$_6$)-alkyl, NH$_2$, NH(C$_1$–C$_6$)-alkyl, N((C$_1$–C$_6$)-alkyl)$_2$, SO$_2$—CH$_3$, COOH, COO—(C$_1$–C$_6$)-alkyl or CONH$_2$);
R4 is (C$_1$–C$_6$)-alkyl, (C$_3$–C$_6$)-cycloalkyl, (C$_2$–C$_6$)-alkenyl, (C$_3$–C$_6$)-alkynyl, phenyl or CH$_2$-phenyl (wherein the phenyl ring may be optionally substituted once or twice by F, Cl, Br, I, OH, CF$_3$, NO$_2$, CN, OCF$_3$, O—(C$_1$–C$_6$)-alkyl, (C$_1$–C$_6$)-alkyl, NH$_2$, NH(C$_1$–C$_6$)-alkyl, N((C$_1$–C$_6$)-alkyl)$_2$, SO$_2$—CH$_3$, COOH, COO—(C$_1$–C$_6$)-alkyl or CONH$_2$);
R5 is H, (C$_1$–C$_6$)-alkyl, (C$_3$–C$_6$)-cycloalkyl, (C$_2$–C$_6$)-alkenyl, (C$_3$–C$_6$)-alkynyl, phenyl or CH$_2$-phenyl (wherein the phenyl ring may be optionally substituted once or twice by F, Cl, Br, I, OH, CF$_3$, NO$_2$, CN, OCF$_3$, O—(C$_1$–C$_6$)-alkyl, (C$_1$–C$_6$)-alkyl, NH$_2$, NH(C$_1$–C$_6$)-alkyl, N((C$_1$–C$_6$)-alkyl)$_2$, SO$_2$—CH$_3$, COOH, COO—(C$_1$–C$_6$)-alkyl or CONH$_2$), or
R4 and R5 together form one of the groups CH$_2$—CH$_2$—CH$_2$—CH$_2$—CH$_2$, CH$_2$—CH$_2$—N(CH$_3$)—CH$_2$—CH$_2$, CH$_2$—CH$_2$—N(CH$_2$-phenyl)-CH$_2$—CH$_2$, CH$_2$—CH$_2$—O—CH$_2$—CH$_2$ or CH$_2$—CH$_2$—CH$_2$—CH$_2$; and R6 is (C$_1$–C$_6$)alkyl, acyl, (C=O)—(C$_1$–C$_6$)alkyl, (C=O)—(C$_3$–C$_6$)-cycloalkyl, phenyl, naphthyl, pyridyl, —SO$_2$-phenyl, or SO$_2$-naphthyl;
and their physiologically tolerated salts.

2. The method of claim 1, wherein
Y is a direct linkage, CH$_2$ or CH$_2$—CH$_2$;
X is CH$_2$ or O;
R1 is F, Cl, Br, I, CF$_3$, CN, NO$_2$, COOH, COO(C$_1$–C$_6$) alkyl, CONH$_2$, CONH(C$_1$–C$_6$)alkyl, CON((C$_1$–C$_6$) alkyl)$_2$, (C$_1$–C$_6$)-alkyl, (C$_2$–C$_6$)-alkenyl, (C$_2$–C$_6$)-alkynyl, O—(C$_1$–C$_6$)-alkyl (wherein one, more than one or all hydrogen(s) in the alkyl, alkenyl and alkynyl radicals may be replaced by fluorine, or one hydrogen may be replaced by OH, OC(O)CH$_3$, OC(O)H, O—CH$_2$—Ph, NH$_2$, NH—CO—CH$_3$ or N(COOCH$_2$Ph)$_2$), SO$_2$—NH$_2$, SO$_2$—NH(C$_1$–C$_6$)-alkyl, SO$_2$—N((C$_1$–C$_6$)-alkyl)$_2$, S—(C$_1$–C$_6$)-alkyl, S(CH$_2$)$_n$-phenyl, SO—(C$_1$–C$_6$)-alkyl, SO—(CH$_2$)$_n$-phenyl, SO$_2$—(C$_1$–C$_6$)-alkyl, SO$_2$—(CH$_2$)$_n$-phenyl (wherein n is 0–6 and the phenyl radical may be substituted up to two times by F, Cl, Br, OH, CF$_3$, NO$_2$, CN, OCF$_3$, O—(C$_1$–C$_6$)-alkyl, (C$_1$–C$_6$)-alkyl or NH$_2$), phenyl or O-phenyl (wherein the phenyl radical may be optionally substituted up to two times by F, Cl, Br, I, OH, CF$_3$, NO$_2$, CN, OCF$_3$, O—(C$_1$–C$_6$)-alkyl, (C$_1$–C$_6$)-alkyl, NH$_2$, NH(C$_1$–C$_6$)-alkyl, N((C$_1$–C$_6$)-alkyl)$_2$, SO$_2$—CH$_3$, COOH, COO—(C$_1$–C$_6$)-alkyl or CONH$_2$);
R1' is H, F, Cl, Br, I, CF$_3$, CN, NO$_2$, COOH, COO(C$_1$–C$_6$) alkyl, CONH$_2$, CONH(C$_1$–C$_6$)alkyl, CON((C$_1$–C$_6$) alkyl)$_2$, (C$_1$–C$_6$)-alkyl, (C$_2$–C$_6$)-alkenyl, (C$_2$–C$_6$)-alkynyl, O—(C$_1$–C$_6$)-alkyl (wherein one, more than one or all hydrogen(s) in the alkyl, alkenyl and alkynyl radicals may be replaced by fluorine, or one hydrogen may be replaced by OH, OC(O)CH$_3$, OC(O)H, O—CH$_2$—Ph, NH$_2$, NH—CO—CH$_3$ or N(COOCH$_2$Ph)$_2$), SO$_2$—NH$_2$, SO$_2$NH(C$_1$–C$_6$)-alkyl, SO$_2$N((C$_1$–C$_6$)-alkyl)$_2$, S—(C$_1$–C$_6$)-alkyl, S—(CH$_2$)$_n$-phenyl, SO—(C$_1$–C$_6$)-alkyl, SO—(CH$_2$)$_n$-phenyl, SO$_2$—(C$_1$–C$_6$)-alkyl, SO$_2$—(CH$_2$)$_n$-phenyl (wherein n is 0–6 and the phenyl radical may be substituted up to two times by F, Cl, Br, OH, CF$_3$, NO$_2$, CN, OCF$_3$, O—(C$_1$–C$_6$)-alkyl, (C$_1$–C$_6$)-alkyl or NH$_2$), phenyl or O-phenyl (wherein the phenyl radical may be optionally substituted up to two times by F, Cl, Br, I, OH, CF$_3$, NO$_2$, CN, OCF$_3$, O—(C$_1$–C$_6$)-alkyl, (C$_1$–C$_6$)-alkyl, NH$_2$, NH(C$_1$–C$_6$)-alkyl, N((C$_1$–C$_6$)-alkyl)$_2$, SO$_2$—CH$_3$, COOH, COO—(C$_1$–C$_6$)-alkyl or CONH$_2$);

R2 is NH$_2$, NHR3 or NR4R5, wherein
R3 is (C$_1$–C$_6$)alkyl, CN, CHO, CO—NH$_2$, CH=NH, C(S)—NH$_2$, C(=NH)—NH-phenyl (wherein the phenyl ring may be optionally substituted up to two times by F, Cl, Br, I, OH, CF$_3$, NO$_2$, CN, OCF$_3$, O—(C$_1$–C$_6$)-alkyl, (C$_1$–C$_6$)-alkyl, NH$_2$, NH(C$_1$–C$_6$)-alkyl, N((C$_1$–C$_6$)-alkyl)$_2$, SO$_2$—CH$_3$, COOH, COO—(C$_1$–C$_6$)-alkyl or CONH$_2$), phenyl or CH$_2$-phenyl (wherein the phenyl ring may be optionally substituted up to 3 times by F, Cl, Br, I, OH, NO$_2$, CN, OCF$_3$, O—(C$_2$–C$_6$)-alkyl, (C$_2$–C$_6$)-alkyl, NH$_2$, NH(C$_1$–C$_6$)-alkyl, N((C$_1$–C$_6$)-alkyl)$_2$, SO$_2$—CH$_3$, COOH, COO—(C$_1$–C$_6$)-alkyl or CONH$_2$);
R4 is (C$_1$–C$_6$)-alkyl, (C$_3$–C$_6$)-cycloalkyl, (C$_2$–C$_6$)-alkenyl, (C$_3$–C$_6$)-alkynyl, phenyl or CH$_2$-phenyl (wherein the phenyl ring may be optionally substituted once or twice by F, Cl, Br, I, OH, CF$_3$, NO$_2$, CN, OCF$_3$, O—(C$_1$–C$_6$)-alkyl, (C$_1$–C$_6$)-alkyl, NH$_2$, NH($C_1$–$C_6$)-alkyl, N(($C_1$–$C_6$)-alkyl)$_2$, SO$_2$—CH$_3$, COOH, COO—($C_1$–$C_6$)-alkyl or CONH$_2$);

R5 is ($C_1$–$C_6$)-alkyl, ($C_3$–$C_6$)-cycloalkyl, ($C_2$–$C_6$)-alkenyl, ($C_3$–$C_6$)-alkynyl, phenyl or CH$_2$-phenyl (wherein the phenyl ring may be optionally substituted once or twice by F, Cl, Br, I, OH, CF$_3$, NO$_2$, CN, OCF$_3$, O—($C_1$–$C_6$)-alkyl, ($C_1$–$C_6$)-alkyl, NH$_2$, NH($C_1$–$C_6$)-alkyl, N(($C_1$–$C_6$)-alkyl)$_2$, SO$_2$—CH$_3$, COOH, COO—($C_1$–$C_6$)-alkyl or CONH$_2$), or R4 and R5 together form one of the groups CH$_2$—CH$_2$—CH$_2$—CH$_2$—CH$_2$, CH$_2$—CH$_2$—N(CH$_3$)—CH$_2$—CH$_2$, CH$_2$—CH$_2$—N(CH$_2$-phenyl)-CH$_2$—CH$_2$, CH$_2$—CH$_2$—O—CH$_2$—CH$_2$ or CH$_2$—CH$_2$—CH$_2$—CH$_2$; and R6 is ($C_1$–$C_6$)alkyl, acyl, (C═O)—($C_1$–$C_6$)alkyl, (C═O)—($C_3$–$C_6$)-cycloalkyl, phenyl, naphthyl, pyridyl, —SO$_2$-phenyl, or SO$_2$-naphthyl;

and their physiologically tolerated salts.

3. The method of claim 1, wherein:

Y is a direct linkage;

X is CH$_2$;

R1 is F, Cl, Br, CF$_3$, CN, ($C_1$–$C_6$)-alkyl, O—($C_1$–$C_6$)-alkyl (wherein one, more than one or all hydrogen(s) in the alkyl radicals may be replaced by fluorine), SO$_2$—NH$_2$, SO$_2$NH($C_1$–$C_6$)-alkyl, SO$_2$N(($C_1$–$C_6$)-alkyl)$_2$, SO$_2$—($C_1$–$C_6$)-alkyl, SO$_2$—(CH$_2$)$_n$-phenyl (wherein n is 0–6 and the phenyl radical may be substituted up to two times by F, Cl, Br, OH, CF$_3$, NO$_2$, CN, OCF$_3$, O—($C_1$–$C_6$)-alkyl, ($C_1$–$C_6$)-alkyl or NH$_2$), phenyl, O-phenyl (wherein the phenyl radical may be optionally substituted up to two times by F, Cl, Br, OH, CF$_3$, NO$_2$, CN, OCF$_3$, O—($C_1$–$C_6$)-alkyl, ($C_1$–$C_6$)-alkyl), or pyridyl;

R1' is H, F, Cl, Br, CF$_3$, CN, ($C_1$–$C_6$)-alkyl, O—($C_1$–$C_6$)-alkyl (wherein one, more than one or all hydrogen(s) in the alkyl radicals may be replaced by fluorine), SO$_2$—NH$_2$, SO$_2$NH($C_1$–$C_6$)-alkyl, SO$_2$N(($C_1$–$C_6$)-alkyl)$_2$, SO$_2$—($C_1$–$C_6$)-alkyl, SO$_2$—(CH$_2$)$_n$-phenyl (wherein n is 0–6 and the phenyl radical may be substituted up to two times by F, Cl, Br, OH, CF$_3$, NO$_2$, CN, OCF$_3$, O—($C_1$–$C_6$)-alkyl, ($C_1$–$C_6$)-alkyl or NH$_2$), phenyl (wherein the phenyl radical may be optionally substituted up to two times by F, Cl, Br, OH, CF$_3$, NO$_2$, CN, OCF$_3$, O—($C_1$–$C_6$)-alkyl or ($C_1$–$C_6$)-alkyl) or pyridyl;

R2 NH$_2$, NHR3 or NR4R5, wherein

R3 is ($C_1$–$C_6$)alkyl, CN, CHO, CO—NH$_2$, CH═NH, C(S)—NH$_2$, C(═NH)—NH-phenyl (wherein the phenyl ring may be optionally substituted up to two times by F, Cl, Br, OH, CF$_3$, NO$_2$, CN, OCF$_3$, O—($C_1$–$C_6$)-alkyl, ($C_1$–$C_6$) alkyl, NH$_2$, NH($C_1$–$C_6$)-alkyl or N(($C_1$–$C_6$)-alkyl)$_2$);

R4 is ($C_1$–$C_6$)-alkyl;

R5 is ($C_1$–$C_6$)-alkyl; or

R4 and R5 together form a CH$_2$—CH$_2$—CH$_2$—CH$_2$—CH$_2$— group;

and their physiologically tolerated salts.

4. The method of claim 1, further comprising administering one or more anorectic active ingredient(s).

5. The method of claim 2, further comprising administering one or more anorectic active ingredient(s).

6. The method of claim 3, further comprising administering one or more anorectic active ingredient(s).

7. The method of claim 1, wherein the pharmaceutical composition comprises a dose in the range of 0.3 mg to 100 mg/per day/per kg of body weight.

8. The method of claim 7, wherein the pharmaceutical composition comprises a dose in the range of 3 mg to 50 mg/per day/per kg of body weight.

9. The method of claim 1, wherein the pharmaceutical composition is in the form of a soft gelatin capsule.

10. The method of claim 8, wherein the soft gelatin capsule comprises 100 mg of a compound of formula (I).

11. The method of claim 1, wherein the pharmaceutical composition is in the form of an emulsion.

12. The method of claim 10, wherein the emulsion comprises 60 mg of a compound of formula (I) per ml.

13. The method of claim 1, wherein the pharmaceutical composition is in the form of a rectal suppository.

14. The method of claim 12, wherein the rectal suppository comprises 40 mg of a compound of formula (I).

15. The method of claim 1, wherein the pharmaceutical composition is in the form of a tablet.

16. The method of claim 14, wherein the tablet comprises 40 mg of a compound of formula (I).

17. The method of claim 1, wherein the pharmaceutical composition is in the form of a coated tablet.

18. The method of claim 16, wherein the coated tablet comprises 50 mg of a compound of formula (I).

19. The method of claim 1, wherein the pharmaceutical composition is in the form of a hard gelatin capsule.

20. The method of claim 18, wherein the hard gelatin capsule comprises 100 mg or 140 mg of a compound of formula (I).

21. The method of claim 1, wherein the pharmaceutical composition is in the form of liquid drops.

22. The method of claim 21, wherein the liquid drops comprises 100 mg of a compound of formula (I) in 1 ml of drops.

23. The method of claim 9, wherein the soft gelatin capsule comprises about 100 mg of a compound of formula (I).

24. The method of claim 11, wherein the emulsion comprises about 60 mg of a compound of formula (I) per 5 ml dose.

25. The method of claim 13, wherein the rectal suppository comprises about 40 mg of a compound of formula (I).

26. The method of claim 15, wherein the tablet comprises about 40 mg of a compound of formula (I).

27. The method of claim 17, wherein the coated tablet comprises about 50 mg of a compound of formula (I).

28. The method of claim 19, wherein the hard gelatin capsule comprises about 100 mg or about 140 mg of a compound of formula (I).

29. The method of claim 22, wherein the liquid drops comprises about 100 mg of a compound of formula (I) in 1 ml of drops.

* * * * *